Figure 1:
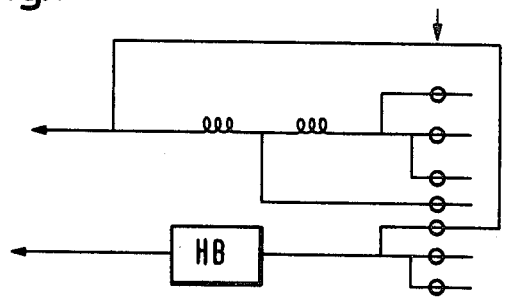

United States Patent [19]

Klose et al.

[11] 4,102,742

[45] Jul. 25, 1978

[54] PROCESS FOR ENZYMATIC ANALYSIS

[75] Inventors: Sigmar Klose, Berg, Starnberger; Alexander Hagen, Tutzing, both of Germany

[73] Assignee: Boehringer Mannheim GmbH, Mannheim-Waldhof, Germany

[21] Appl. No.: 692,701

[22] Filed: Jun. 3, 1976

[30] Foreign Application Priority Data

Jun. 13, 1975 [DE] Fed. Rep. of Germany ...... 2526558

[51] Int. Cl.² ............................................ G01N 31/14
[52] U.S. Cl. ....................... 195/103.5 R; 195/103.5 C
[58] Field of Search ................................. 195/103.5 R

[56] References Cited
U.S. PATENT DOCUMENTS

| 3,838,011 | 9/1974 | Hagen et al. | 195/103.5 R |
| 3,953,296 | 4/1976 | Trutnovsky et al. | 195/103.5 R |

Primary Examiner—Alvin E. Tanenholtz
Assistant Examiner—C. A. Fan
Attorney, Agent, or Firm—Burgess, Dinklage & Sprung

[57] ABSTRACT

Process for enzymatic analysis by the enzymatic reaction of a substance to be determined and measurement of the increase or decrease of a reaction component of the main reaction or subsequent reaction, comprising adding to a solution which contains dissolved therein the enzyme necessary for the reaction, a sample solution containing a substance to be determined, measuring a particular reaction component, and then circulating the enzyme solution through a reactor which completely removes the measured reaction component from the solution (or converts it to a non-disturbing product) and again mixing the enzyme solution, if necessary after replenishing the used up components, with a new sample solution.

12 Claims, 4 Drawing Figures

HB = HEATING BATH

HB = HEATING BATH
R = REACTOR (CHARCOAL)

HB = HEATING BATH
D = DIALYZER

HB = HEATING BATH
D = DIALYZER
R = REACTOR (CARRIER BOUND LDH)

PROCESS FOR ENZYMATIC ANALYSIS

The present invention is concerned with a method for carrying out enzymatic analyses. More specifically, the invention relates to enzymatic analyses capable of being carried out, and particularly suitable for, in automatic analysis devices.

In the analysis of natural systems, such as biological fluids, and especially in clinical chemistry, it is necessary to deal with a test material which contains a plurality of substrates, some of which are chemically very similar. It has been shown that, in many processes, the use of enzymes is necessary in order to ensure the necessary specificity and thus the freedom from disturbance of a substrate determination. Enzymes act as catalysts, i.e., they are not used up during the reaction. This fact led to the consideration as to how these enzymes, some of which are very expensive, can, after a reaction has been concluded, again be used in another analysis.

A material which has proved to be particularly well suited for this purpose is an enzyme fixed on to an inert, insoluble carrier material: this solid material is either removed from the reaction solution after the analysis, for example by filtration, or the reaction solution is allowed to flow through a reactor which contains this solid material. From this, it also follows that the use of carrier-bound enzymes takes place the most simply and effectively in automatic analysis devices and especially in those with a continuous flow-through.

In the case of automatic analysis devices in which reagent flows through continuously, carry over is one of the main problems. Due to adsorption of the substrate or of products resulting therefrom on the walls of the flow system, it can happen that portions are carried over from a sample in the solution region in which the subsequent sample is present. This effect must be kept as small as possible. In the case of conventional and widely used processes, this could be achieved by only employing glass or special plastic tubes as material through which the solutions flow between the sample vessel and the analyzer.

The main disadvantage of the use of an enzyme reactor with carrier-bound enzyme therein placed ahead of the measurement device is that the problem of carry over is hereby considerably increased and is frequently very difficult to overcome. Thus, the sample frequency and the period of analysis are substantially fixed in the case of automatic analysis devices. In most automatic analysis devices, a frequency of 60 per hour is the lower limit. On the other hand, especially in the case of devices which have several channels in parallel, such as the so-called SMA ® apparatus (determination of up to 12 different substrates), the reaction time should be less than 10 minutes since the methods already present on the apparatus lie below this reaction time and since the results of all channels must be indicated simultaneously. Therefore, very high specific activities are necessary in the case of carrier-bound enzymes in order that the reactor can be kept small and carry over minimized.

In practice, it has frequently proved to be difficult to make available in the reactor an activity of enzyme bound to carriers which is sufficiently high and, on the other hand, to permit the required high sample frequency. The enzymatic activity increases directly proportionally with the surface area of the material with which the reaction solution comes into contact. On the other hand, however, on a large surface area, which, in the micro-region, must, in the case of enzymatically-active material, be regarded as being porous and spongy, more substrate and products resulting therefrom will be absorbed than in the case of a material with a smaller surface area. This means that falsification of the results of a subsequent sample becomes greater due to carry over. From this, it follows that, in the case of large surface areas, the washing out process between samples must be more intensive, i.e. must be prolonged, which is only possible at the expense of the sample frequency.

A further disadvantage of such a procedure, i.e., the use of an enzyme reactor before the analyzer, is that some enzymes can admittedly be fixed but, nevertheless, their catalytic activity cannot or almost cannot exert itself, since a direct contact with the substrate cannot be obtained. This applies to substrates such as the triglycerides which are present in lipophilic microphases, whereas the lipases necessary for the splitting thereof are present on the carrier in hydrophilic surroundings. In this way, a contact between enzyme and substrate is made very difficult, if not impossible.

The present invention substantially overcomes the above-mentioned difficulties and reduces the amount of enzyme used in the analytical processes, especially in the case of processes carried out in automatic analysis devices, with the use of a dissolved enzyme for reaction of the substrate to be determined. In particular, the present invention makes the necessary amount of enzyme usable for a series of repeated analyses without this enzyme immobilized for this purpose.

The present invention provides a process for enzymatic analysis by the enzymatic reaction of a substance to be determined and measurement of the increase or decrease of a reaction component of the main or of a subsequent reaction, especially in automatic analysis devices, comprising adding to a solution which contains dissolved therein the enzyme necessary for the reaction (and, if necessary, further enzymes, as well as adjuvants, such as buffers, salts, co-enzymes, color-forming agents and the like) a sample solution containing a substance to be determined, and measuring a particular reaction component circulating the enzyme solution and, after the measurement of the substance to be determined, passing the enzyme solution through a reactor which completely removes the measured reaction component from the solution or converts it into a non-disturbing product and again mixing the enzyme solution thereafter obtained, if necessary after supplementing the used up components, with a sample solution.

Thus, in the process according to the present invention, the enzymes which participate directly in the reactions are not immobilized, i.e., not fixed on to carriers, but are circulated in that the reagents and the enzymes are dissolved and, before mixing with a new sample but after measurement of the substance to be determined, all the reaction products which would disturb or falisfy the next measurement are removed.

The process according to the present invention is preferably used in automatic analysis devices and makes it possible to introduce the reactor, which is thereby necessary, into a place or at a point in the circulation where it can no longer unfavorably influence the sample differentiation which is the case outside the path between the point of introduction of the sample and the point of measurement (analyzer; generally a cuvette). Therefore, neither the shape nor the surface area of the reactor can influence the sample frequency and carry over problems are avoided.

The process according to the present invention can, when used in automatic analysis devices, be employed with or without incorporated dialysis. However, it is preferably used with processes with dialysis in which removal of disturbing reaction products can take place not only in a primary cycle but also in a secondary cycle, for which purpose different reactors are preferably employed.

Therefore, according to a preferred embodiment of the present invention, a reaction product to be measured is, for the measurement, partially dialyzed off from the solution circulation and the portion of this product which is not dialyzed off is converted into a non-disturbing product or is removed.

According to the present invention, the reactor is to be understood to mean a stretch or run in the reaction circulation in which all reaction products which would disturb or falsify the next measurement are removed. This removal can be carried out not only chemically but also physically. Physical removal can take place by adsorption on suitable adsorbents or by photolysis and chemical removal can take place by chemical binding on appropriate materials or by chemical reaction with the formation of non-disturbing products. In the selection of the reactor, particular care is to be paid to the fact that the enzyme flowing in a cycle is not to be adsorbed to any substantial extent. This adsorption can be prevented, for example, by a previous saturation of the reactor with dissolved proteins, such as albumin. However, an initial adsorption during the running-in period is permissible insofar as it comes to a stop after some time. Furthermore, it is important that the disturbing reaction products are quantitatively removed or converted. For this purpose, individual substances of an inorganic or organic nature or mixture of several such materials can be used in the reactor. Within the scope of the present invention, there are preferred either adsorbing substances or carrier-bound enzyme which are able to catalyze the further reaction of the undesired reaction products with the formation of non-disturbing products. Furthermore, the material employed in the reactor is to have the lowest possible degree of solubility in order not to give rise to impurities in the circulating system. In addition, the adsorption and reaction material in the reactor should be such that it substantially maintains its flowthrough properties during the course of the process. Materials which satisfy these requirements can readily be selected without any great difficulties.

Apart from the disturbing reaction products, other substances necessary for the carrying out of the analysis can also be adsorbed or converted. However, it is a prerequisite that the circulating solution can, without difficulty, again be replenished with these used up reagents.

Within the scope of the process according to the present invention, appropriate reactor materials include adsorbents, such as active charcoal, silica gel, fullers' earth, kieselgur, activated aluminum oxide and activated bauxite, especially for the removal of colored materials. The reactor employed according to the present invention preferably contains one or more immobilized enzymes, especially enzymes covalently fixed on to carriers, which are able further to convert the measured reaction product. In the case of this use of carrier-bound enzymes according to the present invention, carry over problems do not arise so that, with regard to the dimensioning of the enzyme reactor, practically no limitations exist. A preferred example of this embodiment of the present invention is the use of carrier-fixed dehydrogenase, such as lactate dehydrogenase (LDH), in the case of reactions which proceed with the formation of reduced nicotinamide-adenine dinucleotide (NADH) and the amount of the latter formed is determined. In the presence of reducible materials, such as pyruvate, the NADH is again converted into nicotinamide-adenine dinucleotide (NAD) and thus is again available for reduction in the next cycle. This embodiment is suitable for very many different substrates which are measured in the UV test with NADH or reduced nicotinamide-adenine dinucleotide phosphate (NADPH), for example for the determination of glucose.

A preferred modification of the process according to the present invention, especially when using carrier-bound enzyme in the reactor, consists in the intermittent returning of the solution in a cycle instead of a continuous return. In the case of intermittent returning, the solution, after measurement of the substance to be determined, is collected in individual fractions and each fraction is individually treated in a reactor until disturbing products have been completely removed. This embodiment is especially advantageous when the activity of the carrier-bound enzyme is relatively low and, therefore, a long period of treatment in the reactor would be necessary in the case of continuous returning. Due to the intermittent returning with several parallel-arranged reactors, the reactor size can be kept small without the period of treatment being shortened.

Another possibility of using the process of the present invention is, for example, in the case of those reactions which proceed with the participation of an oxidase and thus with the formation of hydrogen peroxide. Hydrogen peroxide is usually detected by means of a color reaction. This color reaction can take place in the enzyme circulation, whereby the colored material formed can, after measurement, be removed again, for example by adsorption of the colored material in a wood charcoal reactor. If desired, it is also possible to dialyze off a part of the hydrogen peroxide and only to measure the amount dialyzed off, the amount remaining in the circulation being destroyed by a carrier-bound enzyme, for example carrier-bound catalase.

The process according to the present invention can be carried out in commercially-available automatic analysis apparatus, for example the "AutoAnalyzer ®" devices, but also in devices of other manufacture. Experiments which have been carried out have shown that the dissolved enzymes used in the process according to the present invention can be used again many times and thus the amount of dissolved enzyme needed can be reduced at least by a factor of 10. The reusability of the enzymes is thereby only limited by the gradual accumulation of breakdown products and by the increasing dilution of the solution by the samples introduced.

The volume of the circulating solution can be kept constant by continuously or intermittently separating off excess solvent, for example by reverse osmosis.

The advantages of the process according to the present invention in the case of using carrier-bound enzymes in the reactor include the possibility of using enzymatically-active granulate instead of a tubular reactor, the production of which is substantially more problematical, using several enzymes by mixing granulates, a simultaneous fixing of several enzymes, with its attendant problems, being made superfluous, and arranging the running in procedure for the system in such a manner that no reagents are used up, only reagents but not samples being introduced in the circulation. Furthermore, according to the present invention, the reactors, when they contain immobilized enzymes, can be operated at those temperatures which are the most favorable for the bound enzymes. A deproteinization of the sample is also not necessary. The frequently employed segmentation of the individual samples by air bubbles can also be employed.

The following Examples are given for the purpose of illustrating the present invention.

EXAMPLE 1

Cholesterol Determination

The determination is carried out on a commercially available automatic analysis device with samples segmented by air bubbles.

(a) Conventional Method

The process proceeds according to the following reaction equations:

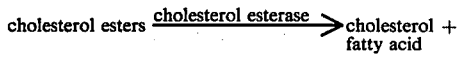

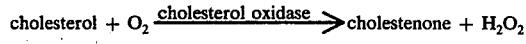

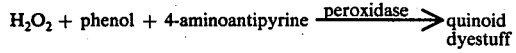

4-Aminopyrine has the structural formula:

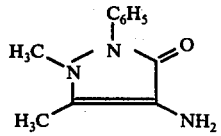

and the quinoid dyestuff formed therefrom has the structural formula:

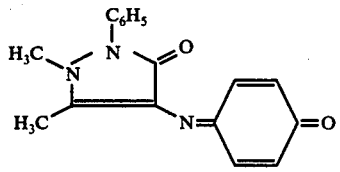

The process is carried out with the use of a solution with the following concentrations and activities:

0.4M potassium phosphate buffer (pH 7.2); 4% methanol (v/v); 0.4% hydroxypolyethoxydodecane; 0.6 mg. 4-aminopyrine/ml.; >0.1 U/ml. cholesterol oxidase; >0.1 U/ml. cholesterol esterase; >2.5 U/ml. peroxidase; 1.2 mg./ml. phenol.

The flow scheme is illustrated in FIG. 1 of the accompanying drawings.

(b) Process According to the Present Invention

The following reagents are employed:

Reagent 1: 0.4 M potassium phosphate buffer (pH 7.2); 4% methanol (v/v); 0.1 U/ml. cholesterol oxidase; 0.1 U/ml. cholesterol esterase; 2.5 U/ml. peroxidase.

Reagent 2: 1.2 g. 4-aminoantipyrine; 0.6 g. phenol; 5 ml. hydroxyethoxydodecane in 100 ml. double distilled water.

Figure 2:
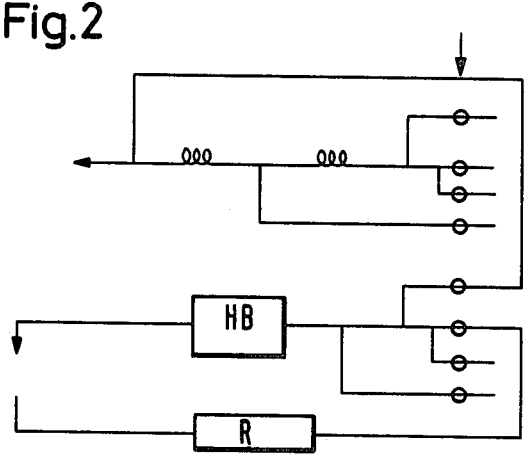

According to the flow scheme illustrated in FIG. 2 of the accompanying drawings, a solution circulation is set up in which is arranged a reactor containing 20 g. wood charcoal. The wood charcoal was incubated for 2 hours in a 6% albumin solution and subsequently placed in a vertically standing column which serves as reactor. The reagent which contains the colored quinoid material formed during the reaction passes through the column. The colored material, as well as 4-aminoantipyrine and also, to a certain extent, phenol and hydroxypolyethoxydodecane, are there absorbed. The enzymes run through without hinderance. Reagent 2 is added continuously in order to maintain the necessary concentrations of phenol, 4-aminoantipyrine and surface-active material.

With this method of working, using 30 ml. of Reagent 1, which in the known process suffice for a 30 minute running time corresponding to 30 determinations, the process can be carried out for 390 minutes without deterioration of the enzyme activity being observed. During this time, 130 aqueous cholesterol standards, each with 50 to 400 mg. cholesterol/100 ml. and 140 serum samples are analyzed with unchanged correctness. The remaining time was used for the observation of the base extinction of the reagents (base line). In this case, no change could be ascertained, from which it follows that the quinoid colored material has been quantitatively absorbed.

In the case of this experiment, the enzymes were reused 13 times and thus the proportion of the enzyme costs, which account for about two-thirds of the costs of this test, were reduced by a factor of 13.

EXAMPLE 2

Glucose Determination by the Hexokinase Method

The determination takes place according to the following reaction equations:

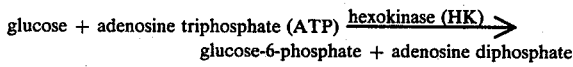

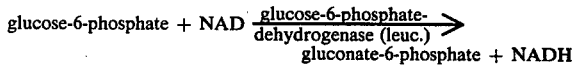

The process was carried out in a commercially available automatic analysis device with dialysis and with segmenting of the samples by means of air bubbles.

(a) Conventional Method

There was used a reagent with the following reactants and activities:

0.075M triethanolamine buffer (pH 7.8); 1 mM magnesium sulphate; 3.5 mM NAD; 0.455 mM ATP: 1 U/ml. HK; 1 U/ml. glucose-6-phosphate-dehydrogenase (G-6-P-DH) (leuc.) 0.1% surface-active agent (polyethyleneglycol ether).

Figure 3:
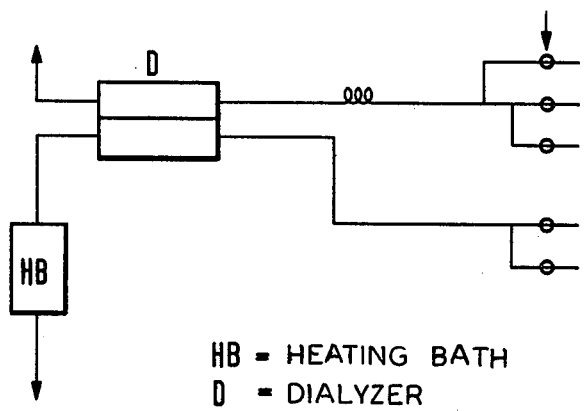

The flow scheme is illustrated in FIG. 3 of the accompanying drawings.

(b) Method According to the Present Invention

Figure 4:
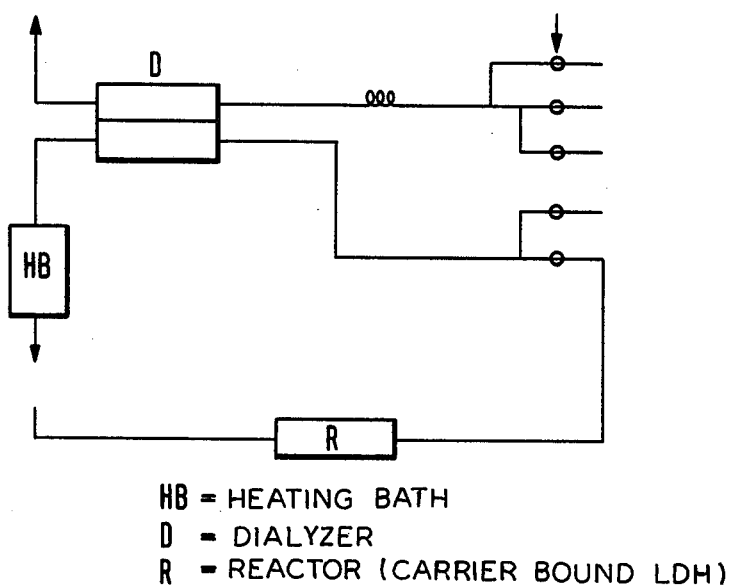

There was used the flow scheme illustrated in FIG. 4 of the accompanying drawings. The following reagents were employed:

Reagent 1: 1 mM tris-(hydroxymethyl)-aminomethane hydrochloride buffer (pH 7.8); 5 mM pyruvate; 0.1% surface-active agent.

Reagent 2: 0.075 M triethanolamine buffer (pH 7.8); 1 mM magnesium sulphate; 3.5 mM NAD; 0.455 mM ATP; 1 U/ml. HK; 1 U/ml. G-6-P-DH (leuc.); 0.1% surface-active agent.

The reactor consisted of a 2 meter long tube on the inner surface of which were fixed about 4 U/m LDH. The following reaction took place in the tube:

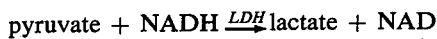

Thus, the NADH formed in dependence upon the glucose concentration was changed back into NAD. The pyruvate needed for the reaction diffuses from the primary cycle by the dialysis.

With 20 ml. of Reagent 2, which in the conventional process only suffice for 20 minutes running time, corresponding to 20 determinations, the process was carried out for 200 minutes. A dropping off of the sensitivity (extinction/100 mg. glucose) was not observed in this period of time. During this time, 96 aqueous standard solutions (of 50 to 400 mg. glucose/100 ml.) and 40 control sera were analyzed with unchanged correctness. The remainder of the time was employed to control the constancy of the base extinction of the reagents (base line).

This process can also be carried out in the same way with other dehydrogenases instead of lactate dehydrogenase.

It will be understood that the specification and examples are illustrative but not limitative of the present invention and that other embodiments within the spirit and scope of the invention will suggest themselves to those skilled in the art.

What is claimed is:

1. Process for the enzymatic analysis of a substance to be determined involving at least one enzymatic reaction of the substance to be determined, which process comprises adding a sample solution containing the substance to be determined to an enzyme solution of at least one enzyme, solvent and other necessary reagents, causing at least one principal enzymatic reaction that produces a reaction product to occur, measuring said reaction product, then passing the enzyme solution containing said reaction product through a reactor containing an adsorbent which completely adsorbs and removes said reaction product from the solution, replenishing any used up reagents in the remaining enzyme solution to form a regenerated enzyme solution, and contacting the regenerated enzyme solution with fresh sample solution.

2. Process as claimed in claim 1 wherein said reaction product is a reaction product of the principal enzymatic reaction occuring upon addition of said sample solution to said enzyme solution.

3. Process as claimed in claim 1 wherein said reaction product is the reaction product of a reaction subsequent to the principal enzymatic reaction.

4. Process as claimed in claim 1 wherein said addition of necessary reagents includes another enzyme or coenzyme.

5. Process as claimed in claim 1 wherein said additional necessary reagents include a color-forming agent.

6. Process as claimed in claim 1 wherein said process is carried out in an automatic analysis device.

7. Process as claimed in claim 6 wherein the samples are segmented by means of air bubbles.

8. Process as claimed in claim 1 wherein said adsorbent is active charcoal, silica gel, fullers' earth, kieselgur, activated aluminum oxide or activated bauxite.

9. Process as claimed in claim 1 wherein the volume of the regenerated enzyme solution is kept constant by continuously or intermittently separating off excess solvent.

10. Process as claimed in claim 9 wherein excess solvent is separated off by reverse osmosis.

11. Process as claimed in claim 1 wherein the enzyme solution is returned intermittently in individual fractions each of which is individually treated in a reactor.

12. Process for the enzymatic analysis of a substance to be determined involving at least one enzymatic reaction of the substance to be determined, which process comprises adding a sample solution containing the substance to be determined to an enzyme solution of at least one enzyme and other necessary reagents, causing at least one enzymatic reaction that produces a reaction product to occur, dialyzing off part of said reaction product contained in the enzyme solution measuring said dialyzed off reaction product, subjecting the remaining portion of the enzyme solution to removal of said reaction product contained therein in a reactor containing an adsorbent which completely removes said reaction product from the enzyme solution, mixing the enzyme solution thereafter and contacting the enzyme solution with fresh sample solution.

* * * * *